United States Patent [19]

Hinsken et al.

[11] 4,338,244

[45] Jul. 6, 1982

[54] BENZOFURAN(2)ONE OR INDOLIN(2)ONE COMPOUNDS USEFUL AS STABILIZERS FOR ORGANIC MATERIALS

[75] Inventors: Hans Hinsken, Kandern, Fed. Rep. of Germany; Horst Mayerhoefer, Oberwil; Wolfgang Mueller, Allschwil, both of Switzerland; Hermann Schneider, Grenzach-Wyhlen, Fed. Rep. of Germany

[73] Assignee: Sandoz Ltd., Basel, Switzerland

[21] Appl. No.: 118,011

[22] Filed: Feb. 4, 1980

[30] Foreign Application Priority Data

Feb. 5, 1979 [CH] Switzerland .................. 1104/79
Sep. 28, 1979 [CH] Switzerland .................. 8793/79

[51] Int. Cl.$^3$ .................. C08K 5/15; C08K 5/34
[52] U.S. Cl. .................. 524/109; 524/111; 524/94
[58] Field of Search .................. 260/45.8 A, 45.8 N

[56] References Cited

U.S. PATENT DOCUMENTS

| | | | |
|---|---|---|---|
| 3,325,499 | 6/1967 | Poos | 260/45.8 N |
| 3,370,063 | 2/1968 | Suh | 260/45.8 N |
| 3,428,649 | 2/1969 | Plostnieks | 260/45.8 N |
| 3,577,430 | 5/1971 | Plostnieks | 260/45.8 N |
| 3,862,133 | 1/1975 | Layer | 260/45.8 A |
| 4,080,360 | 3/1978 | Schlichting et al. | 260/45.8 N |
| 4,132,703 | 1/1979 | Crochemore et al. | 260/45.8 A |

*Primary Examiner*—John Kight, III
*Assistant Examiner*—R. A. White
*Attorney, Agent, or Firm*—Gerald D. Sharkin; Robert S. Honor; Joseph J. Borovian

[57] ABSTRACT

The present invention relates to a process for stabilizing organic polymeric materials comprising incorporating therein a benzofuran(2)one compound or indolin(2)one compound containing at least two benzofuran(2)one or indolin(2)one nuclei.

24 Claims, No Drawings

BENZOFURAN(2)ONE OR INDOLIN(2)ONE COMPOUNDS USEFUL AS STABILIZERS FOR ORGANIC MATERIALS

The present invention relates to a process for stabilizing organic polymeric materials employing benzofuranone or indolinone compounds as stabilisers.

Accordingly, the present invention provides a process for stabilising organic polymeric materials comprising incorporating therein a benzofuran(2) one or indolin(2)one compound contain at least two benzofuran(2)one or indolin(2)one nuclei, respectively.

Preferred benzofuran(2)one compounds and indolin(2)one compounds for use in the process of the present invention are bis-benzofuran(2)one or bis-indolin(2)one compounds in which the 3-position of the first benzofuran(2)one or indolin(2)one nucleus is bound directly to the 3- or 7-position of the second benzofuran(2)one or indolin(2)one nucleus, respectively, or the 5-, 6- or 7-position of the first benzofuran(2)one or indolin(2)one nucleus is bound directly to the same position of the second nucleus, and benzofuran(2)one or indolin(2)one compounds in which the 3-, 5-, 6-, or 7-position of the benzofuran(2)one or indolin(2)one nucleus is attached to the same position of 1 to 5 further such nuclei through a 2 to 6 valent bridge member.

Preferred directly bound bis-benzofuran(2)ones and bis-indolin(2)ones are those of formula $I_a$,

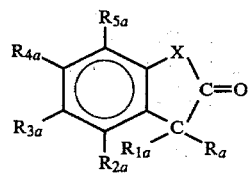

$I_a$ in which X is —O— or

$-NR_{10a}$ either, $R_a$ is hydrogen or (aa/1)

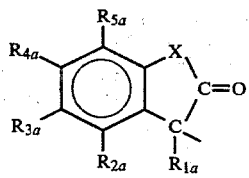

(aa/1)

and each $R_{1a}$, independently, is hydrogen; $C_{1-22}$alkyl; $C_{5-6}$-cycloalkyl; $C_{1-5}$alkyl$C_{5-6}$-cycloalkyl; phenyl; phenyl substituted by a total of up to three substituents selected from the group consisting of $C_{1-12}$alkyl (up to three of these with max. 18 carbon atoms in the combined alkyl substituents), hydroxyl (max. of two of these), $C_{1-12}$alkoxy, $C_{1-18}$acyloxy, chlorine and nitro (max. of one of each of these); a group of formula (a/4), (a/5) or (a/6)

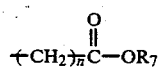

(a/4)

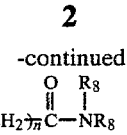

(a/5)

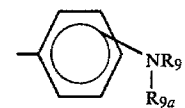

(a/6)

or, $R_a$ together with $R_{1a}$ is (a/3)

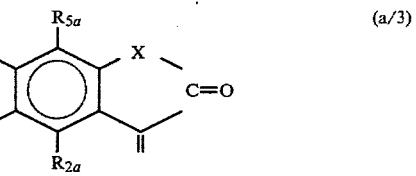

(a/3)

or, $R_a$ is hydrogen and $R_{1a}$ is (a/7)

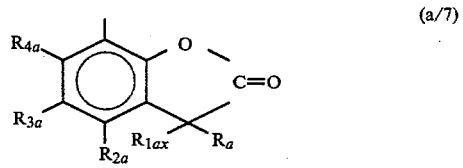

(a/7)

with the proviso that when $R_{1a}$ is (a/7) X is —O—, $R_{1ax}$ is phenyl or phenyl substituted by a total of up to three substituents selected from the group consisting of $C_{1-12}$alkyl (max. three of these with a total of up to 18 carbon atoms in the combined alkyl substituents), hyroxyl (max. two of these), $C_{1-12}$alkoxy, $C_{1-18}$acyloxy, chlorine and nitro (max. one of each of these), and $R_{2a}$ to $R_{5a}$, independently, is hydrogen; $C_{1-12}$alkyl; max. two of $R_{3a}$ to $R_{5a}$ are: $C_{5-6}$cycloalkyl; $C_{1-5}$alkyl-$C_{5-6}$cycloalkyl; hydroxyl; $C_{1-22}$alkoxy; phenoxy optionally substituted by up to two $C_{1-12}$alkyl groups with a total of up to 16 carbon atoms in the combined alkyl substituents; $C_{1-18}$acyloxy; phenylcarbonyloxy; chlorine; max. one of $R_{3a}$ to $R_{5a}$ is: phenyl-$C_{1-9}$alkyl or phenylthio in which the phenyl nucleus is optionally substituted by up to three substituents selected from $C_{1-12}$alkyl, hydroxyl, and $R_{15}CO$—O—; phenyl optionally substituted by up to two $C_{1-12}$alkyl groups with a total of up to 16 carbon atoms in the combined substituents; nitro;

 (b/2);

 (b/3) as $R_{3a}$

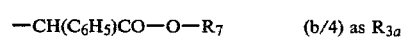 (b/4) as $R_{3a}$

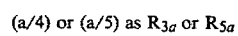 (a/4) or (a/5) as $R_{3a}$ or $R_{5a}$ with the proviso that when $R_{11}$ in (b/2) is other than hydrogen such (b/2) group is adjacent a hydroxyl group, or, when $R_a$ is hydrogen, $R_{1a}$ is other than (a/7) and X is —O—, $R_{3a}$ is ($E_3$) or $R_{5a}$ is ($E_5$)

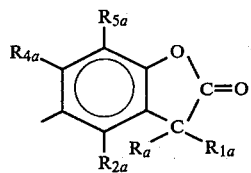
(E3)

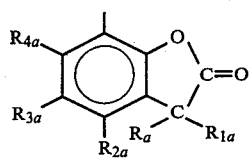
(E5)

each
independently, is hydrogen; $C_{1-18}$alkyl; alkyl-O-alkylene with a total no. of up to 18 carbon atoms; alkyl-S-alkylene with a total no. of up to 18 carbon atoms; di-$C_{1-4}$alkylamino$C_{1-8}$alkyl; $C_{5-7}$cycloalkyl; or phenyl optionally substituted by up to 3 $C_{1-12}$alkyl groups with a total no. of up to 18 carbon atoms in the combined substituents, either, each $R_8$, independently, is hydrogen; $C_{1-18}$alkyl; $C_{5-6}$cycloalkyl; $C_{1-5}$alkyl-$C_{5-6}$cycloalkyl; phenyl optionally substituted by up to two $C_{1-12}$alkyl groups with max. 16 carbon atoms in the combined substituents;

—CH$_2$CH$_2$OH  (d/1);

—CH$_2$CH$_2$OC$_{1-18}$alkyl  (d/2); or

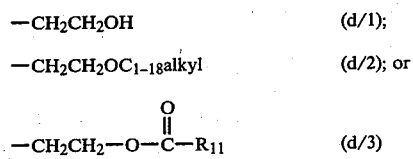  (d/3)

or, both $R_8$ together with the nitrogen form piperidine or morpholine, $R_9$ has one of the significances of $R_8$, $R_{9a}$ is hydrogen, $C_{1-18}$alkyl, (d/1), (d/2) or (d/3), $R_{10a}$ is hydrogen, $C_{1-18}$alkyl, $C_{5-6}$cycloalkyl, $C_{1-5}$alkyl-$C_{5-6}$cycloalkyl or phenyl optionally substituted by up to two $C_{1-12}$alkyl groups with max. 16 carbon atoms in the combined substituents, or benzyl, $R_{11}$ is hydrogen, $C_{1-22}$alkyl, $C_{5-7}$cycloalkyl, phenyl$C_{1-6}$alkyl or phenyl optionally substituted by up to two $C_{1-12}$alkyl groups with max. 16 carbon atoms in the combined substituents, $R_{12}$ is $C_{1-18}$alkyl, 2-hydroxyethyl, phenyl or $(C_{1-9})$alkylphenyl, $R_{15}$ is $C_{1-22}$alkyl or phenyl, and n is 0, 1 or 2, and the molecule contains only two benzofuran(2)one or indolin(2)one nuclei, whereby the substituents on the two benzofuran(2)one or indolin(2)one nuclei are the same or different, preferably they are the same.

Of the directly bound benzofuran(2)ones and indolin(2)ones, the benzofuran(2)one compounds are preferred.

Preferred poly-benzofuran(2)ones or indolin(2)ones linked by a bridging group are those in which the bridging group is bound to the 3-, 5- or 7-position of the benzofuran(2)one or indolin(2)one nucleus.

When the bridging group is attached to the 3-position of the benzofuran(2)one or indolin(2)one nucleus, such group may be bound via a single or double bond.

Preferred bridged benzofuran(2)one or indolin(2)one compounds are those of formula $I_b$,

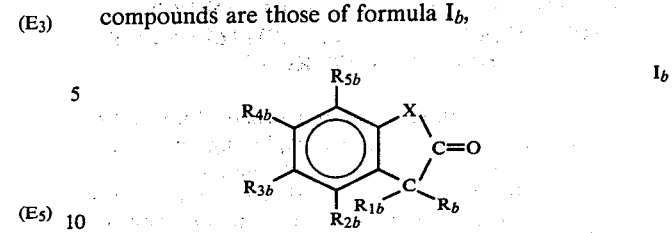
$I_b$ in which —X— is as defined above, $R_b$, $R_{1b}$, $R_{2b}$, $R_{3b}$, $R_{4b}$ and $R_{5b}$ correspond to the significances $R_a$, $R_{1a}$, $R_{2a}$, $R_{3a}$, $R_{4a}$ and $R_{5a}$ above with the exception tht the molecule is free from groups of formulae (aa/1), (a/3), (a/7), (E3) and (E5) and either $R_{1b}$, or $R_b$ and $R_{1b}$ together, or $R_{3b}$, or $R_{5b}$ is bound to one or more further corresponding benzofuran(2)one or indolin(2)one nuclei through a polyvalent bridge member.

Preferred groups in place of $R_{1b}$ are:

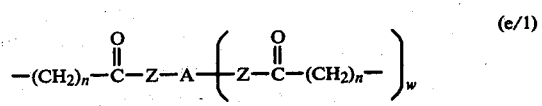
(e/1)

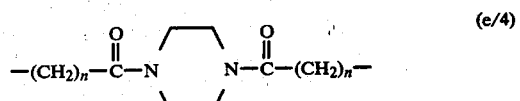
(e/4)

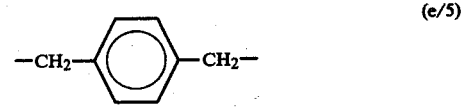
(e/5)

(e/6)
—$C_mH_{2m}$—

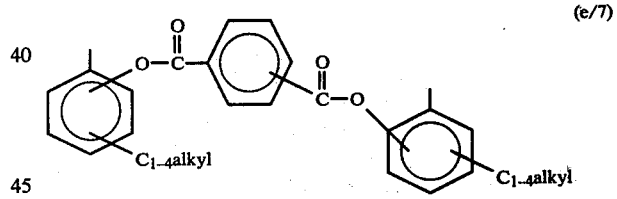
(e/7)

(e/7a)

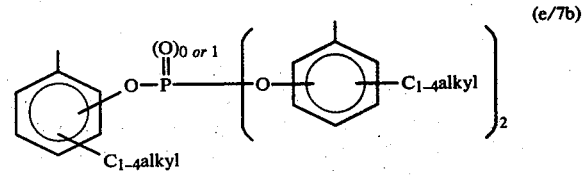
(e/7b)

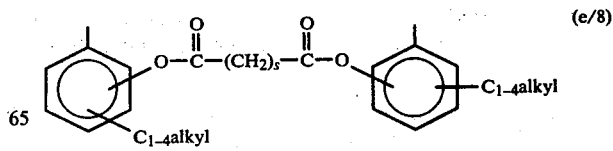
(e/8)

in which the free valencies are attached to groups $E_1$

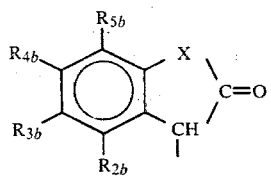

E₁

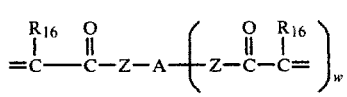 (e/9)

=HC—(C_pH_{2p})—CH= (e/12)

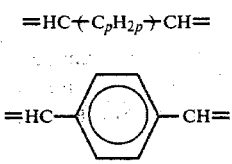 (e/13)

A is a 2 to 6 valent saturated alkylene which optionally contains sulphur, oxygen, nitrogen or cyclohexylene bridges or is a 2- or 3-valent benzene radical or when both Z's are —O—, A is also (e/16)

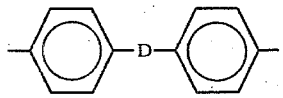 (e/16)

in which the free valencies are attached to groups $E_{1a}$

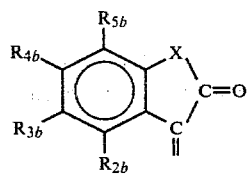 $E_{1a}$ whereby when A is a 3-, 4-, 5- or 6-valent radical the further valencies are bound to OH, —NHR₁₀ or

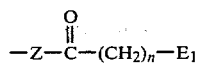

and

A, Z, w and R₁₀ are as defined above, with the exception that on A the further free valencies are attached to —OH, —NHR₁₀ or groups, with the proviso that any free valencies on nitrogen in A itself are attached to

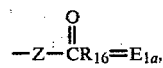

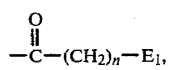, and any free valencies on nitrogen, in A itself are attached to w is from 1 to 6, each Z, independently, is —O— or

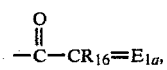,

, p is 0 or 1 to 10, and
R₁₆ is hydrogen or methyl.
Preferred groups in place of R₃b are: —O—, —S—, —SO₂—, >C=O or R₁₀ has one of the significances of R₁₀a above or R₁₀ together with the N-atom signifies

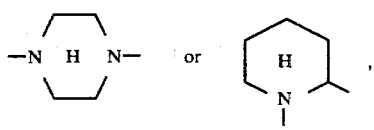

in which R₁₃ is as defined above, or (e/1), or (e/4) in which the free valencies are attached to groups $E_{3b}$ D is a direct bond or —O—, —S—,

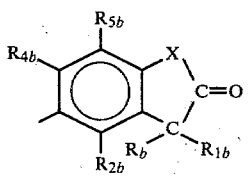 E₃b

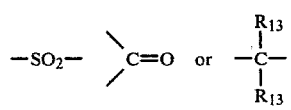

in which each R₁₃, independently, is hydrogen, C₁₋₁₆alkyl (preferably C₁₋₄alkyl) with the proviso that when both R₁₃ are alkyl the combined groups contain max. 16 carbon atoms, phenyl, (a/4) or (a/5);
n is as defined above,
m is 2 to 10, and
s is 0 or 1 to 12.
Preferred groups in place of R_b and R₁b together are:

and A, w, Z and R₁₀ are as defined above, with the exception that on A the further free valencies are attached to —OH, —NHR₁₀ or

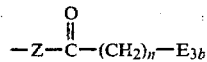

and any free valencies on nitrogen in A itself are attached to

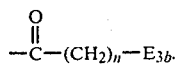

Preferably when $R_{3b}$ is a bridging group bound to one or more $E_{3b}$ nuclei, X is —O— in all cases.

Preferred groups in place of $R_{5b}$ are: —S— or

in which $R_{13}$ is as defined above, or (e/1), or (e/4) in which the free valencies are attached to groups $E_{5b}$

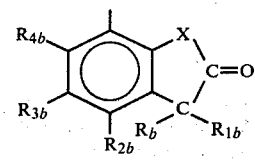

and A, w, Z and $R_{10}$ are as defined above, with the exception that the further free valencies on A are attached to —OH, —NHR$_{10}$ or

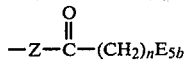

and any N-free valencies in A itself are attached to

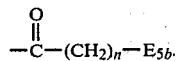

Preferably when $R_{5b}$ is a bridging group bound to $E_{5b}$, X is —O— in all cases.

Examples of 2-valent —Z—A—Z— groups are:

—Z(CH$_2$)$_{n1}$—Z— where $n_1$ is 2 to 12,

—O(CH$_2$CH$_2$O)$_{\overline{1,2\,or\,3}}$CH$_2$CH$_2$O—  —OCH$_2$CH$_2$SCH$_2$CH$_2$O—, —OCH$_2$CH$_2$S—SCH$_2$CH$_2$O—, 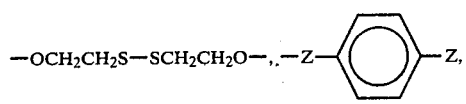

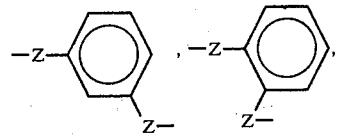

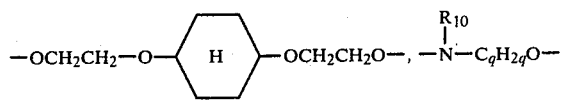

-continued where q is 2 or 3, 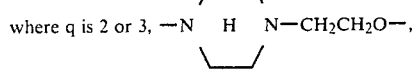

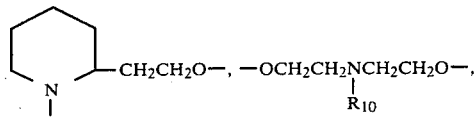

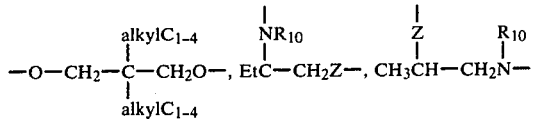

Examples of 3 valent —Z—A—Z— groups are:

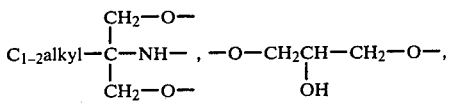

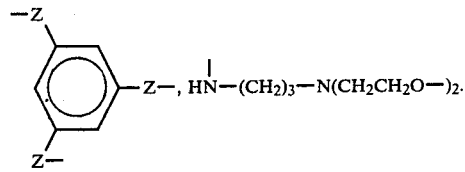

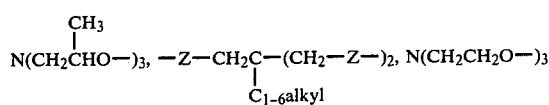

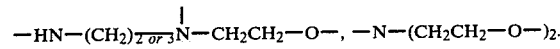

Examples of 4 valent —Z—A—Z— groups are:

(—OCH$_2$)$_4$—C, —NHCH$_2$CH$_2$NCH$_2$CH$_2$NCH$_2$CH$_2$O—,

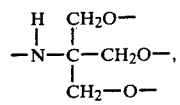

An Example of 5-valent —Z—A—Z— groups is:

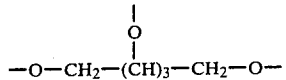

Examples of 6-valent —Z—A—Z— groups are:

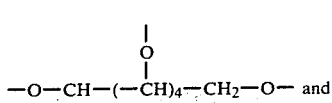 and

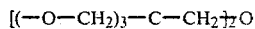

A is preferably 2-, 3- or 4-valent with the following —Z—A—Z— groups being most preferred:
—Z—(CH$_2$)$_{n1}$—Z— with n$_1$=2 to 6 or 10

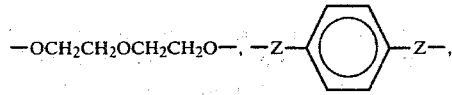

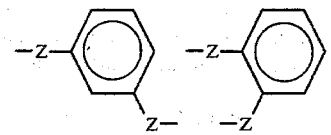

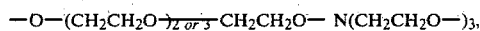

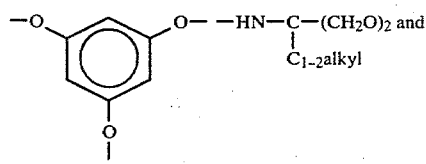

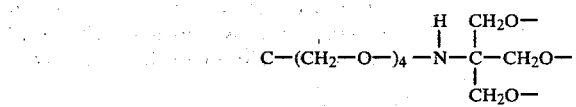

especially those in which A is alkylene.

Most preferred Z—A—Z groups are: C(CH$_2$—O—)$_4$ and —O—(CH$_2$)$_{n1}$O— with n$_1$=2 to 6 or 10 s is preferably 0 to 10 more preferably, 0 to 8.

m is preferably 2 to 6.

p is preferably 2 or 3, more preferably 3.

When R$_{1b}$ is a bridge member carrying one or more benzofuran(2)one or indolin(2)one nuclei it is preferably R$_{1b}'$ where R$_{1b}'$ is (e/1), (e/4),(e/6), (e/7), (e/7a), (e/7b) or (e/8) more preferably (e/7) or (e/8).

When R$_{1b}$ and R$_b$ together form a bridge member carrying one or more benzofuran(2)one or indolin(2)one nuclei they preferably form (e/9) or (e/13), When R$_{3b}$ is a bridge member carrying one or more benzofuran(2)one groups it is preferably R$_{3b}'$, where R$_{3b}'$ is —S— or

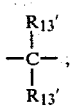

(e/1) or (e/4), where each R$_{13}'$, independently, is hydrogen, C$_{1-4}$alkyl or (a/4) in which R$_7$ is hydrogen, C$_{1-18}$alkyl, with the proviso that when one R$_{13}'$ is (a/4) the other R$_{13}'$ is other than (a/4) preferably methyl. More preferably R$_{3b}$ as a bridging member carrying one or more benzofuran(2)one nuclei, is R$_{3b}''$ where R$_{3b}''$ is

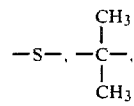

—CH$_2$—, —CH$_2$— (e/1) or (e/4), especially (e/1).

When R$_{5b}$ is a bridge member carrying one or more benzofuran(2)one groups it is preferably R$_{5b}'$ where R$_{5b}'$ is

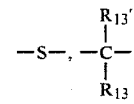

where R$_{13}'$ is as defined above or (e/1). More preferably R$_{5b}$ as a bridge member is R$_{5b}''$, where R$_{5b}''$ is —S— or —CH$_2$—.

In the compounds of formula I$_b$ the substituents on each benzofuran(2)one or indolin(2)one nucleus are the same or different, preferably they are the same.

Of the benzofuran(2)one or indolin(2)one compounds having a bridge member bound to further such nuclei, the benzofuran(2)one compounds are preferred.

R$_a$ is preferably R$_a'$, where R$_a'$ is hydrogen or (aa/1) with (aa/1) being most preferred. In (aa/1) preferably R$_{1a}$ to R$_{5a}$ have the preferred significances as stated herein.

In (a/7), R$_{1ax}$, R$_{2a}$, R$_{2a}$, R$_{3a}$ and R$_{4a}$ preferably have the preferred significances stated herein.

In (a/3) preferably R$_{2a}$ to R$_{5a}$ have the preferred significances stated herein.

R$_{1a}$ is preferably R$_{1a}'$, where R$_{1a}'$ is (a/7) or R$_1'$, where R$_1'$ is hydrogen, C$_{1-18}$alkyl, phenyl optionally substituted by one or two C$_{1-8}$alkyl groups and/or a hydroxyl group; (a/4) or (a/5). More preferably R$_{1a}$ is R$_1''$, where R$_1''$ is C$_{1-18}$alkyl or phenyl optionally substituted by one or two (C$_{1-8}$)alkyl groups and/or a hydroxyl group. Most preferably R$_{1a}$ is R$_1'''$, where R$_1'''$ is phenyl optionally substituted by C$_{1-4}$alkyl, with unsubstituted phenyl being most preferred.

R$_{1ax}$ is preferably R$_1''$, most preferably phenyl optionally substituted by C$_{1-4}$alkyl, with unsubstituted phenyl being most preferred.

R$_{2a}$ and R$_{2b}$ are preferably R$_2'$, where R$_2'$ is hydrogen or C$_{1-4}$alkyl, more preferably R$_2''$, where R$_2''$ is hydrogen or methyl, with hydrogen being especially preferred.

In E$_3$ preferably R$_a$, R$_{1a}$, R$_{2a}$, R$_{4a}$ and R$_{5a}$ have the preferred significances stated herewith.

R$_{3a}$ is preferably R$_a'$, where R$_{3a}'$ is E$_3$ or R$_3'$, where R$_3'$ is hydrogen or C$_{1-9}$ (preferably C$_{1-5}$)alkyl. Most preferably R$_{3a}$ is R$_3'$.

R$_{4a}$ and R$_{4b}$ are preferably R$_4'$, where R$_4'$ is hydrogen or C$_{1-4}$alkyl, with hydrogen being especially preferred.

In E$_5$ preferably R$_a$ and R$_{1a}$ to R$_{4a}$ have the preferred significances stated herein.

R$_{5a}$ is preferably R$_{5a}'$, where R$_{5a}'$ is E$_5$ or R$_5'$, where R$_5'$ is hydrogen or C$_{1-8}$(preferably C$_{1-5}$)alkyl. More preferably R$_{5a}$ is R$_5'$.

R$_b$ is preferably R$_b'$ where R$_b'$ is hydrogen or together with R$_{1b}$ is (e/9) or (e/13).

R$_{1b}$ is preferably R$_{1bx}$, where R$_{1bx}$ is either R$_1'$, more preferably R$_1''$ especially phenyl, or R$_{1b}'$, especially with the preferred A groups in (e/1) and with s as 0 to 8 in (e/8).

$R_{3b}$ is preferably $R_{3bx}$, where $R_{3bx}$ is hydrogen, $C_{1-9}$alkyl or $R_{3b}'$, more preferably hydrogen, methyl or $R_{3b}''$ $R_{5b}$ is preferably $R_{5bx}$, where $R_{5bx}$ is hydrogen, $C_{1-8}$alkyl or $R_{5b}'$, more preferably hydrogen or $R_{5b}''$. X is preferably —O— or

where $R_{10a}'$ is hydrogen, $(C_{1-12})$alkyl, phenyl or benzyl, more preferably, hydrogen, $(C_{1-4})$alkyl or phenyl. Most preferably X is —O—.

$R_{10}$ is preferably $R_{10}'$, where $R_{10}'$ is hydrogen, $(C_{1-12})$alkyl or phenyl, more preferably hydrogen or $(C_{1-4})$alkyl, especially hydrogen or methyl.

$R_7$ is (a/4) and (b/4) is preferably $R_7'$ where $R_7'$ is hydrogen, $C_{1-18}$alkyl, phenyl optionally substituted by up to two $C_{2-12}$alkyl groups with max. 16 carbon atoms in the combined substituents. More preferably $R_7$ is $R_7''$, where $R_7''$ is $C_{1-18}$alkyl, phenyl or $C_{1-12}$alkylphenyl. Most preferably $R_7$ is $C_{1-18}$alkyl, especially $C_{8-18}$alkyl.

Each $E_8$, independently, is preferably $R_8'$, where $R_8'$ is hydrogen, $C_{1-18}$alkyl or both $R_8$'s together form morpholine or piperidine. More preferably each $R_8$, independently is hydrogen or $C_{1-18}$alkyl. Preferred alkyl groups as $R_8$ are $C_{1-12}$-, preferably $C_{1-8}$-, most preferably $C_{1-4}$alkyl.

$R_9$ is preferably $R_9'$, where $R_9'$ is hydrogen, $C_{1-8}$alkyl or (d/1). More preferably $R_9$ is hydrogen or $C_{1-8}$alkyl. The preferred alkyl as $R_9$ contains 1 to 4 carbon atoms.

$R_{9a}$ is preferably $R_{9a}'$, where $R_{9a}'$ is hydrogen or $C_{1-8}$alkyl. Any alkyl as $R_{9a}$ preferably contains 1 to 1 to 4 carbon atoms.

$R_{11}$ is preferably $R_{11}'$, where $R_{11}'$ is hydrogen, $C_{1-18}$alkyl or phenyl. $R_{11}$ in (b/2) is preferably phenyl.

Any alkyl as $R_{11}$ preferably contain 1 to 17 carbon atoms.

$R_{12}$ is preferably $R_{12}'$, where $R_{12}'$ is $C_{1-12}$alkyl, phenyl or 4-(alkyl $C_{1-9}$)phenyl.

$R_{16}$ is preferably hydrogen.

n in (a/4) or (a/5) as $R_1$ or $R_5$ is preferably 1.

n in (a/4) or (a/5) as $R_3'$ is preferably 2.

Preferred compounds of formula $I_a$, are those in which X is —O— $R_a$ is $R_a'$, $R_{1a}$ is $R_{1a}'$, $R_{2a}$ is $R_2'$, preferably $R_2''$, $R_{3a}$ is $R_{3a}'$, $R_{4a}$ is $R_4'$ and $R_{5a}$ is $R_{5a}'$ with the proviso that the molecule contains two and only two directly bound benzofuran(2)one nuclei.

More preferred compounds of formula $I_a$ are those in which $R_a$ is (aa/1), both $R_{1a}$'s are $R_1''$, more preferably $R_1'''$, especially phenyl, $R_{2a}$ is hydrogen, $R_{3a}$ is $R_3'$, preferably hydrogen, $R_{4a}$ is hydrogen, $R_{5a}$ is $R_5'$, and X is —O— and each benzofuran(2)one nucleus is identical.

When $R_{3b}$ is a bridge member carrying further benzofuran(2)one nuclei preferably $R_2$ and $R_4$ are both hydrogen and $R_{5b}$ is hydrogen or $C_{1-4}$alkyl, especially hydrogen.

When $R_{5b}$ is a bridge member carrying further benzofuran(2)one nuclei preferably $R_{3b}$ is hydrogen or $C_{1-8}$alkyl.

Preferred compounds of formula $I_b$ are those in which $R_b$ is $R_b'$, $R_{1b}$ is $R_{1bx}$, $R_{2b}$ is $R_2'$, preferably $R_2''$, $R_{3b}$ is $R_{3bx}$, $R_{4b}$ is $R_4'$, $R_{5b}$ is $R_{5bx}$ and X is —O—, and preferably each benzofuran(2)one nucleus is identical, with the proviso that only one bridge member bearing one or more benzofuran(2)one nuclei is present in the molecule.

More preferred compounds of formula $I_b$ are those in which $R_b$ is $R_b'$, $R_{1b}$ is $R_{1bx}$, $R_{2b}$ is hydrogen, $R_{3b}$ is hydrogen, methyl or $R_{3b}''$, $R_{4b}$ is hydrogen, $R_{5b}$ is hydrogen or $R_{5b}''$, X is —O— and each benzofuran(2)one nucleus is identical.

The directly bound bis benzofuran(2)one or indolin(2)one compounds are either known or may be preferred in accordance with known methods from available starting materials.

The bridged benzofuran(2)one and indolin(2)one compounds as defined above are new and also form part of the present invention.

The bridged benzofuran(2)ones and indolin(2)ones of the invention may be prepared by conventional methods. For example, by condensing a polyfunctional bridge member with appropriately substituted benzofuran(2)ones or indolin(2)ones or by condensation and ring closure reactions of for example, hydroxy substituted bridged benzenes, and by interconversion reactions.

For example compounds of formula $I_b$ in which one of $R_1$, $R_3$ or $R_5$ is (e/1) or (e/4), may be prepared by reacting a corresponding monomeric benzofuran(2)one compound or indolin(2)one compound in which one of $R_1$, $R_3$ and $R_5$ is

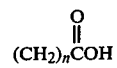

or a functional derivative thereof with a compound H—Z—A—(Z—H)$_w$ compound or with a di-or tri-aminobenzene or with a di- or tri-hydroxybenzene or for (e/4) with piperazine in known manner. Preferred functional derivatives are acid chlorides and lower alkylesters.

Compounds of formula $I_b$ in which $R_1$ is (e/5) or (e/6) may be prepared by reacting a corresponding monomeric benzofuran(2)one or indolin(2)one compound in which R and $R_1$ are both hydrogen with a compound of formula

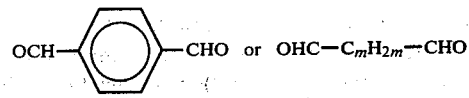

following by catalytic hydration in accordance with known methods.

Similarly, the compounds of formula $I_b$ in which R and $R_1$ together form (e/9), (e/12) or (e/13) may be prepared by reacting the corresponding monomeric benzofuran(2)one or indolin(2)one compound where R and $R_1$ are both hydrogen with the corresponding aldehyde of each of the bridge members.

The compounds of formula $I_b$ in which $R_1$ is (e/7), (e/7a) (e/7b) or (e/8) can be prepared by reacting the corresponding monomeric benzofuran(2)one or indolin(2)one compound in which $R_1$ is 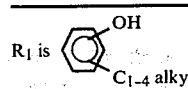

with HOOC—⬡—COOH    for (e/7) or a functional derivative thereof, with HOOC—(CH$_2$)$_s$—COOH    for (e/8) or a functional derivative thereof, with COCl$_2$    for (e/7a), and -continued

| with $[O]_{0.1}$ PCl$_3$ | for (e/7b), |
| --- | --- | in accordance with known methods. Preferred functional derivatives are acid chlorides.

The compounds of formula I$_b$, in which R$_{3b}$ is

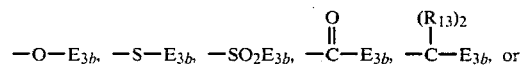

R$_{5b}$ is —S—E$_{5b}$ or 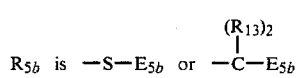

by reacting a compound of formula III or IV

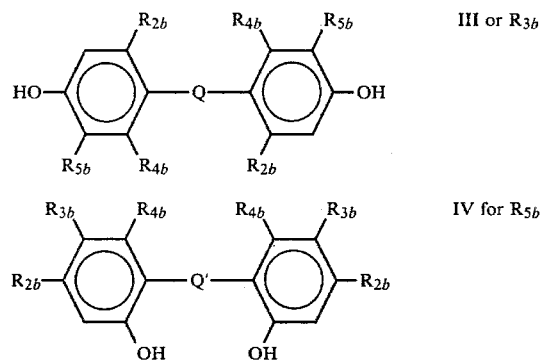

with a compound of formula

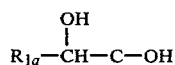

in a 1:2 molar ratio,
where
Q is —O—, —S$_1$—, —SO$_2$—, C═O or

Q$_1$ is —S— or

and
R$_{1a}$ is optionally substituted phenyl as given for R$_{1b}$ above, by known methods.

The compounds of formula I$_b$ in which R and R$_1$ are both hydrogen may be prepared by reacting a compound of formula V

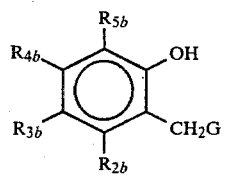

in which R$_{2b}$ to R$_{5b}$ are as defined above and one of R$_{3b}$ or R$_5$ is a bridge member as defined above linked to a further such phenolic compound, and with the exception that in any group (a/4) or (b/4), R$_7$ is hydrogen, and R$_{3b}$ and R$_{5b}$ are other than (a/5), G is a secondary amine group or halogen, with an ionic cyanide compound, hydrolysing the product thereof, followed by a ring closure condensation.

G is preferably —N(C$_{1-4}$alkyl)$_2$, morpholine or piperidine, especially —N(CH$_3$)$_2$. Any halogen as G is preferably chlorine or bromine, especially chlorine. Suitable ionic cyanide compounds are alkali- or alkaline earth cyanides, preferably sodium- or potassium cyanide. Each of the reaction steps may be carried out in accordance with known methods for such reactions.

The end product may be esterified or etherified to obtain compounds where R$_7$ is other than hydrogen. Furthermore, the methylene group in the 3-position may be reacted further to obtain compounds where R$_1$ is other than hydrogen.

The compounds of formula III, IV and V are either known or may be prepared by known methods from available starting materials. The same applies for the other starting materials.

The directly bound bis-benzofuran(2)ones, bis-indolin(2)one and bridged benzofuran(2)ones or indolin(2)ones as defined above (hereinafter referred to as compounds K) may be incorporated into the polymeric material to be stabilized before, during, or after polymerization.

The amount of compound K incorporated may vary according to the material to be stabilized and the ultimate use to which it is to be put. Suitable amounts are from 0.01 to 5% preferably from 0.05 to 1%, based on the weight of the materials to be stabilized. The organic polymeric materials to be stabilized may be natural or synthetic polymeric materials. Examples of such materials include rubber, polyolefins, especially polyethylene, polypropylene, ethylene, propylene copolymers, polybutylene, polystyrene, chlorinated polyethylene, PVC, polyester, polycarbonate, polymethylmethacrylate, polyphenyleneoxide, polyamides such as nylon, polyurethanes, polypropyleneoxide, phenol-formaldehyde resins, epoxy resins, polyacrylonitrile and corresponding copolymers such as acrylonitrile butadiene styrene (ABS) terpolymers.

The process of the present invention is preferably employed to stabilise polypropylene, polyethylene, ethylene/propylene copolymers, PVC, polyesters, polyamides, polyurethanes, polyacrylontrile, ABS terpolymers, terpolymers of acrylic ester, styrene and acrylonitrile, copolymers of styrene and acrylonitrile, styrene/butadiene copolymers, polybutylene and polystyrene. The most preferred organic polymeric materials are polypropylene, polyethylene especially HDPE, ethylene/propylene copolymers and ABS.

The incorporation of the compounds K in the material to be stabilized is effected in accordance with known methods. Preferred methods are those in which the compounds K are incorporated in the polymeric material by melt blending the stabiliser and the additives in conventional equipments such as Banbury mixers, extruders etc. Polypropylene and polyethylene granulates on powders are advantageously employed, whereby the compounds of formula I are admixed with said powders and then extruded etc and worked into the films, foils, bands threads etc.

The process of the present invention may be carried out by incorporating a compound K alone or together with other additives e.g. further stabilisers etc.

The preferred process according to the present invention comprises incorporating a compound K and either (i) a stabiliser of the sterically hindered phenol type, or (ii) a sulphur-containing or phosphorus containing stabiliser, or (i) and (ii), into the polymeric material.

The ratio of stabiliser (i) or (ii) to the compounds K incorporated in the polymeric material is suitably 5:1 to 1:5, preferably 2:1 to 1:1. The ratio of combined (other) stabilisers to compounds K is suitably 15:1 to 1:5, preferably 6:1 to 1:3. Preferably, when only stabilisers (i) are employed with the compounds K the ratio of compounds (i) to Compounds K is 3:1 to 1:1.

Examples of sterically hindered phenols are: β-(4-hydroxy-3,5-ditert.-butylphenyl)-propionicacidstearylester, tetrakis[methylene-3(3',5'-ditert.-butyl-4'-hydroxyphenyl)-propionate]-methane, 1,3,3-tris-(2-methyl-4'-hydroxy-5-tert.-butylphenyl)-butane, 1,3,5-tris(4-tert.-butyl-3-hydroxy-2,6-dimethylbenzyl)-1,3,5-triazine-2,4,6-(1H,3H,5H)-trione, bis(4-tert.-butyl-3-hydroxy-2,6-dimethylbenzyl)-dithiolterephthalate, tris(3,5-ditert.-butyl-4-hydroxybenzylisocyanurate, triester of 3,5-di-tert.-butyl-4-hydroxyhydrocinnamic acid with 1,3,5-tris(2-hydroxyethyl)-s-triazin-2,4,6-(1H,3H,5H)-trione, bis[3,3-bis-4'-hydroxy-3-tert.-butylphenyl)-butaneacid]-glycolester, 1,3,5-trimethyl-2,4,6-tris-(3,5-ditert.-butyl-4-hydroxybenzyl)-benzene, 2,2'-methylene bis(4-methyl-6-tert.-butylphenyl) terephthalate, 4,4-methylene-bis-(2,6-ditert.-butylphenol), 4,4'-butylidene-bis(6-tert.-butyl-meta-cresol), 4,4-thio-bis(2-tert.-butyl-5-methylphenol), 2,2'-methylene-bis(4-methyl-6-tert.-butylphenol Examples of sulphur containing stabilisers are distearylthiodipropionate, dilaurylthiodipropionate, tetrakis(methylene-3-hexylthiopropionate)-methane, tetrakis (methylene-3-dodecylthiopropionate)-methane and dioctadecyldisulphide.

Examples of phosphorus containing compounds are trinonylphenylphosphite, 4,9-distearyl-3,5,8,10-tetraoxadiphosphaspiroundecane, tris-(2,4-ditert.-butylphenyl)phosphite and tetrakis(2,4-ditert.butylphenyl)-4,4'-biphenylene diphosphonite.

In addition to the above further stabilisers, U.V. absorbers as described in DOS 2 606 358 e.g. 2-(2'-hydroxyphenyl)-benztriazole, 2-hydroxybenzophenone, 1,3-bis(2-hydroxybenzoyl)benzene, salicylates, cinnamic acid esters, hydroxybenzoic acid esters, sterically hindered amines and oxylic acid diamides. Suitable such compounds are described in DOS 2 606 358.

Metal deactivators for example N,N'-dibenzoylhydrazide, N-benzoyl-N'-salicyloylhydrazide, N,N'-distearylhydrazide, N,N'-bis-[3-(3,5-ditert.-butyl-4-hydroxyphenyl)-propionyl]-hydrazide, N,N'-bis-salicyloylhydrazide, oxalyl bis-(benzylidenehydrazide), N,N'-bis(3-methoxy-2-naphthoyl-)hydrazide, N,N'-di-α-phenoxy-butyloxy (isophthalyl-dihydrazide) may also be incorporated into the polymeric material.

Additional conventional additives may also be employed for example, flame retardants, antistatic agents etc.

Furthermore, an optical brightener may be incorporated in the polymer to be stabilised and so that the distribution of the additives which are intimately admixed with said optical brightener may be ascertained by fluorescence intensity measurements.

The present invention also provides master batches of polymeric organic materials containing 5 to 90%, preferably 20 to 60%, more preferably 20-30% of a compound K. Such master batches may then be admixed with unstabilised polymeric material. It is to be appreciated that such master batches may also contain additional additives such as those stated above.

Polymeric materials containing a compound K are primarily stabilised against degradation during processing. When, of course, other additives such as antioxidants, e.g. above phenols, and U.V. absorbers are also employed together with the compounds K the polymeric material has an enhanced long term stability against thermal- and photoxidative degradation.

The following examples further serve to illustrate the invention. In the examples all parts are by weight, and all temperatures are in degrees Centigrade.

EXAMPLE 1

2.54 parts of the compound of formula

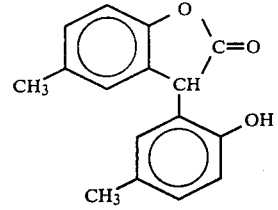

(prepared in accordance with known methods) and 1 part mandelic acid are heated to 200° C. for 16 hours. Afterwards the reaction mixture is separated by column chromatography (silicagel, ether/petroleum ether 1:2). Crystals having a melting point range of 185°–187° C., corresponding to the formula of Compound No. 5 of the Table are obtained.

EXAMPLE 2

78.9 Parts of the compound of formula

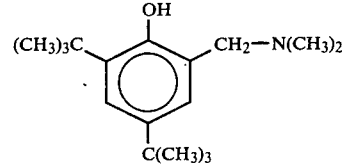

are dissolved in 450 parts diethyleneglycolmonomethylether. 39 Parts potassium cyanide and 6 parts potassium iodide are added thereto. At a temperature of 80° C., 63 parts of water are added dropwise. The temperature is raised to 130° and the mixture is stirred for 16 hours at this temperature. After cooling to room temperature, 1000 parts ice water are added. After carefully acidifying with hydrochloric acid, a precipitate is formed which is dissolved in 400 parts ether. The organic phase is separated, washed with water, dehydrated over MgSO₄ and evaporated. The residue is added to toluene, heated to the boil for approximately 1 hour whereupon water of condensation separates out. After evaporating the solvent and recrystallizing from methanol a colourless crystalline product of formula

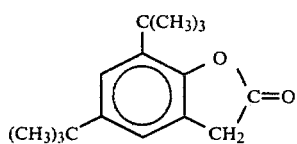

is obtained. A mixture of 19.36 parts of the compound, 5.36 parts terephthalic aldehyde, 0.24 parts piperidine benzoate and 100 parts toluene are heated for 15 hours at reflux temperature. After evaporation of the solvent the product is recrystallized from acetone. The so-obtained crystals are washed with a small amount of ice-cold ether and dried. A yellow powder having a melting point range of 241°–242° C. corresponding to the formula of Compound No. 9, is obtained.

EXAMPLE 3

2,0 Parts pentaerythritol-tetra-[3-(4-hydroxyphenyl)-propionate] and 2,1 parts mandelic acid are heated together to 180° C. for 23 hours. After cooling, the reaction mixture is separated by column chromatography (silicagel, eluent 9:1 toluene/acetone). The so-obtained product has a melting point range of 90°–95° C., and corresponds to the formula of Compound No. 10, Compound Nos. 1, 2 and 4 are made in analogous manner, starting with the corresponding bis phenol compound and reacting the same with mandelic acid.

EXAMPLE 4

A solution of 2,0 parts terephthalic acid dichloride in 40 parts toluene is added slowly at room temperature to a mixture of 5,1 parts of the starting material used in Example 1, 100 parts toluene and 2,1 parts triethylamine. A white precipitate is obtained. The mixture is stirred for some hours at room temperature followed by stirring at 80° C. for 2 hours. The precipitate is filtered off and the clear solution is evaporated. A white crystalline product, melting point 245°–246° C., (recrystallized from acetone/petroleum ether) of the formula of Compound No. 6 is obtained. Compound No. 7 can be prepared in analogous manner.

EXAMPLE 5

1,60 Parts of Compound No. 9 are catalytically dehydrogenated at room temperature under normal pressure. As solvent 20 parts of glacial acetic acid is used, as catalyst 0.2 parts palladium on barium sulfate. After removal of the catalyst and the solvent, the residue is taken up with ether. The etherified solution is shaken with a Na-bicarbonate solution and then with water, followed by dehydrating over MgSO4 and then evaporated. The product, having a melting point range of 258°–259° C. petroleum ether, corresponds to the formula of Compound No. 8. Compound No. 3 of the Table is prepared in accordance with known methods.

No. 1

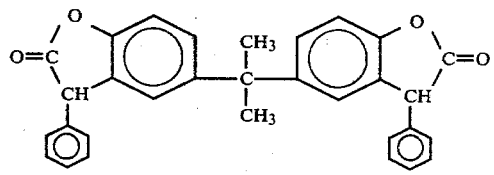

m.pt. 87–188°

No. 2

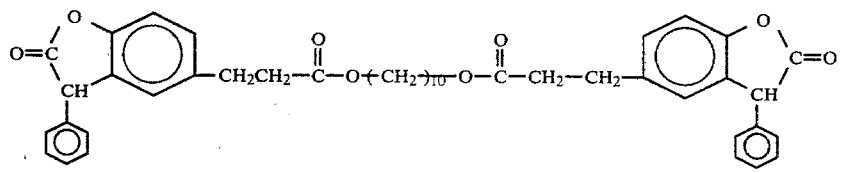

oil

No. 3

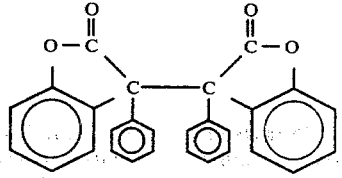

m.pt. 149–150°

No. 4

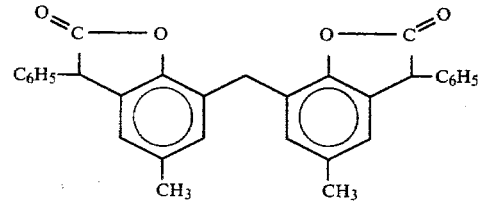

m.pt. 163.6–166° C.

-continued

No. 5
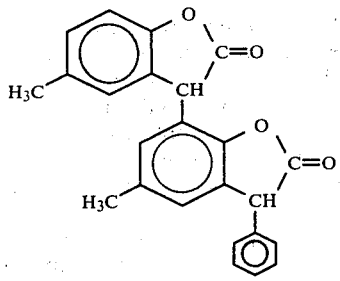
m.pt. 185–187°

No. 6
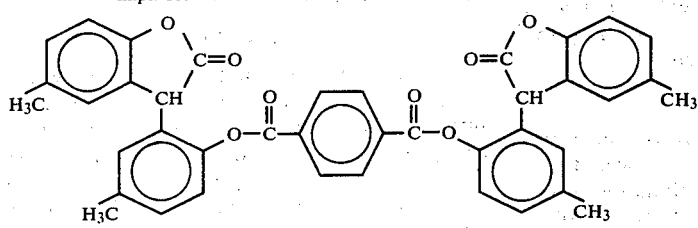
m.pt. 244–5°

No. 7
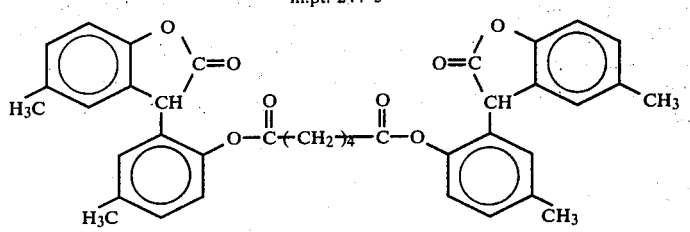
m.pt. 198–202°

No. 8
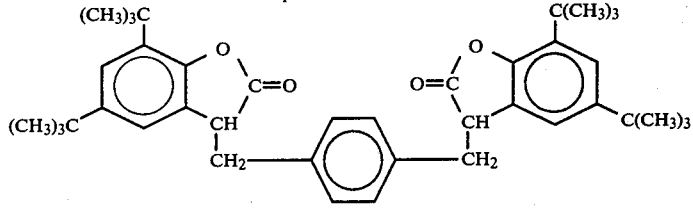
m.pt. 258–9°

No. 9
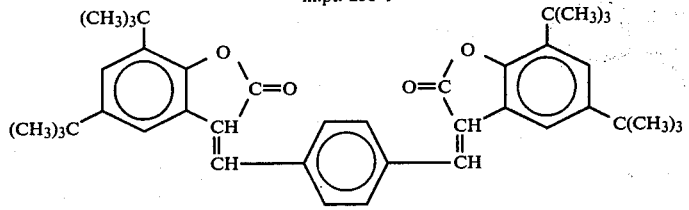
m.pt. 241–242°

No. 10
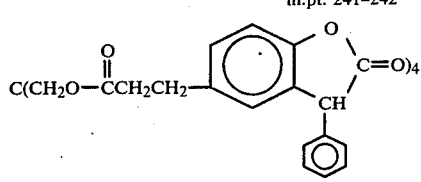
m.pt. 90–95°

EXAMPLE A

A mixture of 1200 parts of a commercially available unstabilized polypropylene (Profax 6501), 0.6 parts calciumstearate, 0.6 parts tetrakis-[methylene-3(3',5'-ditert.-butyl-4'-hydroxyphenyl)-propionate]-methane and 0.6 parts of the Compound No. 8 of the Table are shaken together for 10 minutes and extruded at 120 revs/min with temperatures of 150°, 240°, 260°, and 200° in the different heating areas of the extruder to form a strand which is granulated after passing through a water bath. The granulate is extruded and granulated a further 9 times, each time a part is taken to measure the Melt Flow Index (MFI according to ASTM D 1238 L, 230°; 2.16 kg) which serves as a measure of the thermomechanical oxidative degradation of a polymer. A control without Compound 8 of the Table is also extruded in like manner and tested. In comparison, the polymer containing Compound No. 8 of the Table exhibits a greatly improved melt stability during continuous extrusion. The other compounds of the Table may be employed in like manner.

EXAMPLE B

100 Parts unstabilized HD-polyethylene powder (Phillips Type) are stabilized with 0.02 parts Compound No. 2 of the Table and 0.01 parts tetrakis-[methylene-3(3',5'-di-tert.-butyl-4'-hydroxyphenyl)-propionate)-methane. The powder is subjected to a modified MFI Test at 230°/0.325 kg on a Davenport-MFI apparatus. The powder is pushed into a heated steel cylinder and a 325 g weight is placed thereon. The polymer which is pressed out is cut off at 60 second intervals. The amount is calculated in terms of g/10 min. The stronger the crosslinking of the polymer owing to insufficient stabilization, the lower the MFI value. After 5 to 15 minutes a constant value is obtained. The other compounds of the Tables may be used in analogous manner.

EXAMPLE C 1.0 Part octylstearate, 1.5 parts Ba-Cd stabilizer (powder-forming), 1 part of Compound No. 3 of the Table and 0.5 parts of a commercially available arylalkylphosphate are mixed with 100 parts commercially available dispersion PVC (k-value-60) in a Fluid Mixer (Papenmeier Type TEHK8) until the temperature has risen to 110°. The homogeneous mixture is rolled on rollers heated to 180° for 1 minute and then pressed into plates (thickness 1 mm) at 200° for 1.5 min. at 2 atm. and 1.5 minutes at 20 atm. The test or plates are put into an air circulating drying cabinet at 180° C. for 30 minutes. A comparison sample which contained 2.5 parts Ba-Cd stabilizer instead of Compound No. 3 and 1.5 parts of the Ba-Cd stabilizer was also treated in the same manner. This sample undergoes discolouration even at the beginning of the heat treatment and is markedly more discoloured after the 30 minutes than the sample containing Compound No. 3 of the Table.

EXAMPLE D

300 Parts ABS powder (Fa. Marbon AOE 30/075) are dissolved in 2200 parts chloroform and the solution is dropped into 8000 parts methanol whereupon the ABS is precipitated. After filtration the polymer which is now free from stabilizer is treated in vacuo overnight to remove all the solvent. 100 parts of the so-treated ABS powder is dissolved in chloroform and 0.2 parts Compound No. 2 of the Table are added thereto and the whole is stirred under nitrogen atmosphere for 15 minutes. The solution is drawn into a film with a 1 mm doctor blade onto a glass plate and is left for the solvent to evaporate-off whereby the film shrinks to 150µ thickness and is freed from the rest of the solvent overnight at room temperature in vacuo. The film is then stoved in an air-circulating oven at 95°. By repeated IR-measurement to $\Delta\epsilon=0.4$ at 1715 $cm^{-1}$ the ageing resistance is checked. The samples containing the benzofuranone compound have longer resistance than the control samples which contain no stabilizer.

EXAMPLE E

100 Parts granulated polyethyleneterephthalate are ground to a rough powder and dried overnight at 100° in a vacuum drying cabinet. 1.0 Part of Compound No. 2 of the Table is added and the mixture is homogenised, then granulated in an extruder, spun into fibres at 280°, stretched (120 den/14) and twisted. The fibres are wound on to white cards and exposed to the light in an Atlas Weatherometer for 24 hour intervals. In comparison to a non-stabilized control, the sample containing Compound No. 2 has less tendency to yellow during the exposure to light and can be left in the Weatherometer for a substantially longer period of time in order to reach the same decrease in the tensile strength (50%).

EXAMPLE F

1000 Parts 20% styrene-butadiene rubber emulsion are added with stirring to a hydrochloric acid 5% sodium chloride solution whereupon the rubber coagulates. Stirring is continued for 1 hour at pH 3,5. After filtration the coagulate is repeatedly washed and dried to a constant weight at room temperature in a vacuum cabinet.

25 Parts of this rubber are heated under nitrogen atmosphere to 125° in Brabender plastographs and mixed with 0.25 parts Compound No. 2 of Table 1 for 10 minutes and subsequently pressed to (0.5 mm thick) plates at 125°. The plates were put into an Atlas Weatherometer for 24 hour intervals together with samples containing no stabilizer. In comparison to the latter samples, the stabilized samples exhibited significantly better resistance to light.

EXAMPLE G 49.5 Parts Compound No. 2 of the Table, 49.5 parts tetrakis-[methylene-3-(3',5'-di-tert.-butyl-4'-hydroxyphenyl)propionate]-methane, 1 part calcium stearate and 0.02 parts (7-[24-napthol(1,2d)triazol-2-yl]-3-phenylcumarine (optical brightener) are heated to 140°. The mixture melts with stirring and the melt is poured into a flat dish and ground after cooling. The product obtained melts at 70°–75° C.

0.5 Parts of the ground melt are mixed in a plastic bag by repeated shaking with 1000 parts unstabilized HDPE powder (Ziegler Type, MFI 190/z=0.7). 43 Parts of the powder mixture are heated to 220° in a Brabender PlastiCorder PLV 151 extruder at 50 revs/min. until there is a sharp drop in the torque indicating degradation (to crosslinking decreases). The test sample has good stability.

When different concentrations of the above melt product are mixed with polyethylene or polypropylene powder and extruded into a strand which are subsequently ground, the fluorescence intensity can be measured to assess the distribution of additives in the polymer mixture.

What is claimed is:

1. A process for stabilizing organic polymeric materials comprising incorporating therein a benzofuran(2-)one compound or indolin(2)one compound containing at least two benzofuran(2)one or indolin(2)one nuclei.

2. A process according to claim 1, in which either a bis-benzofuran(2)one or bis-indolin(2)one compound in which the 3-position of the first benzofuran(2)one or indolin(2)one nucleus is bound directly to the 3- or 7-position of the second benzofuran(2)one or indolin(2-)one nucleus, respectively, or the 5-, 6- or 7-position of the first benzofuran(2)one or indolin(2)one nucleus is bound directly to the same position of the second nucleus or a benzofuran(2)one or indolin(2)one compound in which the 3-, 5-, 6- or 7-position of the benzofuran(2-)one or indolin(2)one nucleus is attached to the same position of 1 to 5 further such nuclei through a 2 to 6 valent bridge member is incorporated in the polymeric material.

3. A process according to claim 2 in which the directly bound bis-benzofuran(2)one or bis-indolin(2)one compound is of formula Ia,

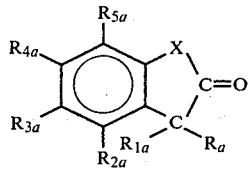
Ia in which X is —O—M or

—NR$_{10a}$, either (i) R$_a$ is (aa/1)

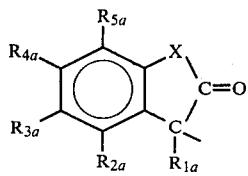
(aa/1)

and each R$_{1a}$, independently, is hydrogen; C$_{1-22}$ alkyl; C$_5$ or C$_6$ cycloalkyl; C$_{1-5}$ alkyl-C$_5$ or C$_6$ cycloalkyl; phenyl; phenyl substituted by one to three substituents selected from the group consisting of C$_{1-12}$ alkyl, hydroxy, C$_{1-12}$ alkoxy, C$_{1-18}$ acyloxy, chloro or nitro, with the provisos that: (1) when the phenyl ring contains more than one C$_{1-12}$ alkyl group, said alkyl groups contain a maximum of 18 carbon atoms, (2) the maximum number of hydroxy substituents is two, and (3) the maximum number of each of the substituents selected from C$_{1-12}$ alkoxy, C$_{1-18}$ acyloxy, chloro and nitro is one; or a group of formula (a/4), (a/5) or (a/6)

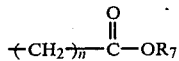
(a/4)

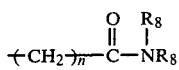
(a/5)

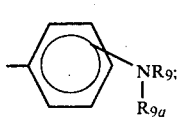
(a/6)

or (ii) R$_a$ together with R$_{1a}$ is a group of formula (a/3)

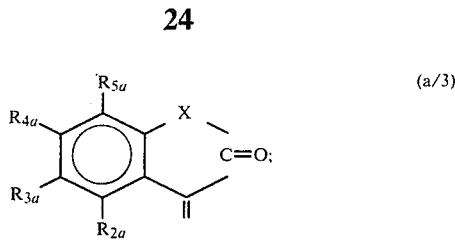
(a/3)

or (iii) R$_a$ is hydrogen, X is —O— and R$_{1a}$ is a group of formula (a/7)

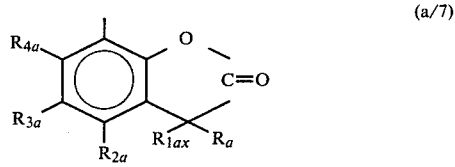
(a/7)

where R$_{1ax}$ is phenyl; or phenyl substituted by one to three substituents selected from the group consisting of C$_{1-12}$ alkyl, hydroxy, C$_{1-12}$ alkoxy, C$_{1-18}$ acyloxy, chloro or nitro, with the provisos that: (1) when the phenyl ring contains more than one C$_{1-12}$ alkyl group, said alkyl groups contain a maximum of 18 carbon atoms, (2) the maximum number of hydroxy substituents is two, and (3) the maximum number of each of the substituents selected from C$_{1-12}$ alkoxy, C$_{1-18}$ acyloxy, chloro and nitro is one; or (iv) R$_a$ is hydrogen, X is —O—, R$_{1a}$ is other than a group of formula (a/7) and either R$_{3a}$ is a group of formula (E$_3$)

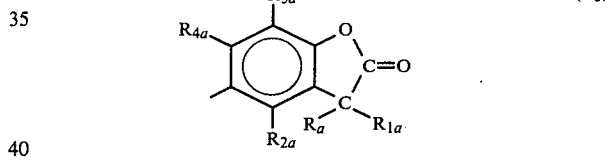
(E$_3$)

or R$_{5a}$ is a group of formula (E$_5$)

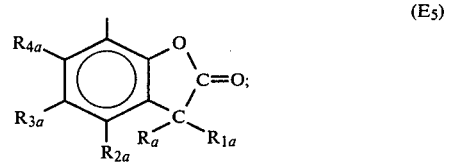
(E$_5$)

each of R$_{2a}$ to R$_{5a}$, independently, is hydrogen; C$_{1-12}$ alkyl; C$_5$ or C$_6$ cycloalkyl; C$_{1-5}$ alkyl-C$_5$ or C$_6$ cycloalkyl; hydroxy; C$_{1-22}$ alkoxy; phenoxy; phenoxy substituted by one or two C$_{1-12}$ alkyl groups, said alkyl groups having a maximum of 16 carbon atoms; C$_{1-18}$ acyloxy; chloro; phenyl-C$_{1-9}$ alkyl; phenylthio; phenyl-C$_{1-9}$ alkyl or phenylthio substituted on the phenyl ring by one to three substituents selected from C$_{1-12}$ alkyl, hydroxy and R$_{15}$CO—O—; phenyl; phenyl substituted by one or two C$_{1-12}$ alkyl groups, said alkyl groups having a maximum of 16 carbon atoms; nitro; a group of formula (b/2), (b/3) or (b/4)

(b/2)

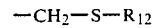
(b/3)

-continued

—CH(C₆H₅)CO—O—R₇; or    (b/4)

a group of formula (a/4) or (a/5) as defined above; with the provisos that:
(a) with respect to the substituents $R_{3a}$, $R_{4a}$ and $R_{5a}$, a maximum of two of said substituents is $C_5$ or $C_6$ cycloalkyl, $C_{1-5}$ alkyl-$C_5$ or $C_6$ cycloalkyl, hydroxy, $C_{1-22}$ alkoxy, optionally substituted phenoxy, $C_{1-18}$-acyloxy or chloro, and only one of said substituents may be optionally substituted phenyl, phenyl-$C_{1-9}$ alkyl or phenylthio, nitro or a group of formula (b/2), (b/3), (b/4), (a/4) or (a/5), provided that only the $R_{3a}$ substituent can be a group of formula (b/3) or (b/4) and only the $R_{3a}$ or $R_{5a}$ substituent can be a group of formula (a/4) or (a/5); and
(b) when $R_{11}$ in the group of formula (b/2) is other than hydrogen, such group is adjacent to a hydroxy group;

each $R_7$, independently, is hydrogen; $C_{1-18}$ alkyl; alkyl-O-alkylene having a maximum of 18 carbon atoms; alkyl-S-alkylene having a maximum of 18 carbon atoms; di-$C_{1-4}$-alkylamino-$C_{1-8}$ alkyl; $C_{5-7}$ cycloalkyl; phenyl; or phenyl substituted by one to three $C_{1-12}$ alkyl groups, said alkyl groups having a maximum of 18 carbon atoms;

either each $R_8$, independently, is hydrogen; $C_{1-18}$ alkyl; $C_5$ or $C_6$ cycloalkyl; $C_{1-5}$ alkyl-$C_5$ or $C_6$ cycloalkyl; phenyl; phenyl substituted by one or two $C_{1-12}$ alkyl groups, said alkyl groups having a maximum of 16 carbon atoms; or a group of formulae (d/1), (d/2) or (d/3)

—CH₂CH₂OH    (d/1)

—CH₂CH₂OC₁₋₁₈ alkyl    (d/2)

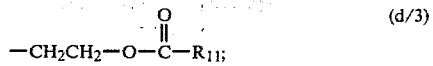    (d/3)

or both $R_8$'s, together with the nitrogen atom, form an unsubstituted piperidine or morpholine ring;
$R_9$ has one of the significances of $R_8$;
$R_{9a}$ is hydrogen; $C_{1-18}$ alkyl; or a group of formula (d/1); (d/2) or (d/3) as defined above;
$R_{10a}$ is hydrogen; $C_{1-18}$ alkyl; $C_5$ or $C_6$ cycloalkyl; $C_{1-5}$ alkyl-$C_5$ or $C_6$ cycloalkyl; phenyl; phenyl substituted by one or two $C_{1-12}$ alkyl groups, said alkyl groups having a maximum of 16 carbon atoms; or benzyl;
$R_{11}$ is hydrogen; $C_{1-22}$ alkyl; $C_{5-7}$ cycloalkyl; phenyl; phenyl-$C_{1-6}$ alkyl; or phenyl or phenyl-$C_{1-6}$ alkyl substituted on the phenyl ring by one or two $C_{1-12}$ alkyl groups, said alkyl groups having a maximum of 16 carbon atoms;
$R_{12}$ is $C_{1-18}$ alkyl; 2-hydroxyethyl; phenyl; or $C_{1-9}$ alkylphenyl;
$R_{15}$ is $C_{1-22}$ alkyl; or phenyl; and n is 0, 1 or 2,
said compound of formula Ia contains only two benzofuran(2)one or indolin(2)one nuclei, wherein the substituents on the two benzofuran(2)one or indolin(2)one nuclei are the same or different; and the bridged polybenzofuran(2)one or poly-indolin(2)one compound is of formula Ib,

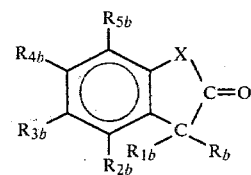    Ib in which X is as defined above, and each of $R_b$, $R_{1b}$, $R_{2b}$, $R_{3b}$, $R_{4b}$ and $R_{5b}$ has the significances corresponding to $R_a$, $R_{1a}$, $R_{2a}$, $R_{3a}$, $R_{4a}$ and $R_{5a}$, respectively, as defined above with the provisos that:
(1) the molecule is free from groups of formulae (aa/1), (a/3), (a/7), (E₃) and (E₅); and
(2) one of $R_{1b}$, $R_b$ and $R_{1b}$ together, $R_{3b}$ or $R_{5b}$ is a polyvalent bridging group linked to one or more further corresponding benzofuran(2)one or indoline(2)one nuclei, said compound of formula Ib contains two or more benzofuran(2)one or indolin(2)one nuclei, wherein the substituents on the benzofuran(2)one or indolin(2)one nuclei are the same or different.

4. A process according to claim 3 in which when $R_{1b}$ is a bridging group linked to one or more further corresponding benzofuran(2)one or indolin(2)one nuclei, it is a group of the formulae,

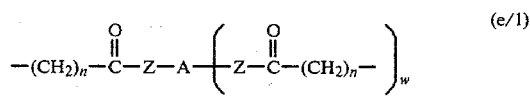    (e/1)

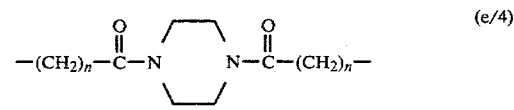    (e/4)

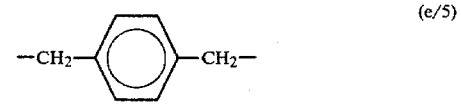    (e/5)

—C_mH_{2m}—    (e/6)

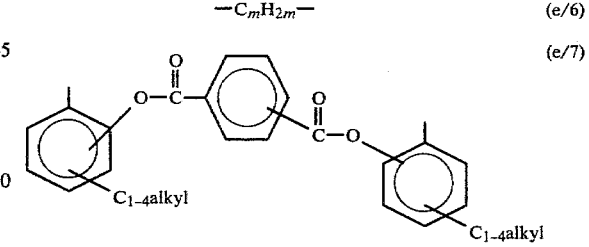    (e/7)

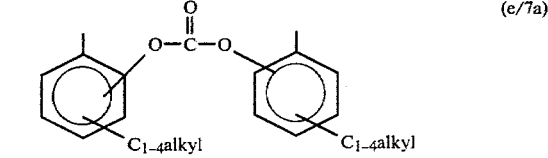    (e/7a)

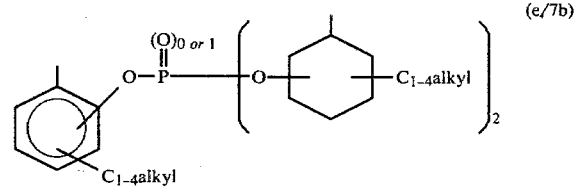    (e/7b)

-continued

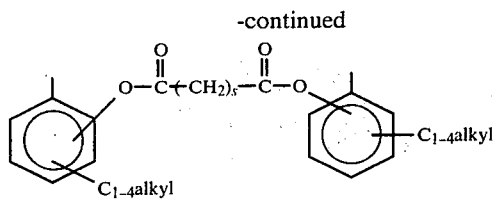
(e/8)

in which the free valencies are attached to one or more groups of the formula $E_1$

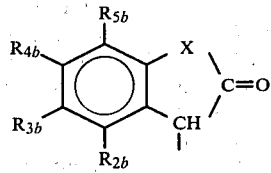
$E_1$ wherein each of X, $R_{2b}$, $R_{3b}$, $R_{4b}$ and $R_{5b}$ is as defined in claim 3, A is a 2 to 6 valent saturated alkylene group; a 2 to 6 valent saturated alkylene group containing one or more bridging members selected from the group consisting of a sulfur atom, an oxygen atom, a nitrogen atom and a cyclohexylene group; a 2- or 3-valent benzene group; or, when both Z's are —O—, is a group of the formula (e/16)

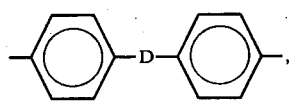
(e/16)

whereby when A is a 3-, 4-, 5- or 6-valent saturated alkylene group, each further free valence is bound to —OH, —NHR$_{10}$ or a group of the formula

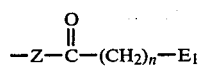

with the proviso that any free valence on nitrogen in A itself is attached to a group of the formula

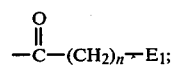

w is an integer 1 to 5;
each Z, independently, is —O— or

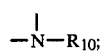

either $R_{10}$ has one of the significances of $R_{10a}$ as defined in claim 3,
or $R_{10}$, together with the nitrogen atom, is a ring of the formula

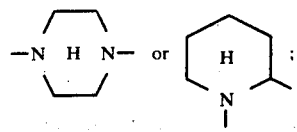

D is a direct bond; —O—; —S—; —SO$_2$—; >C=O; or

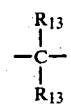

where each $R_{13}$, independently, is hydrogen, $C_{1-16}$ alkyl, phenyl or a group of formula (a/4) or (a/5) as defined in claim 3, with the proviso that when both $R_{13}$'s are $C_{1-16}$ alkyl, the alkyl groups contain a maximum of 16 carbon atoms;
n is as defined in claim 3
m is an integer 2 to 10; and
s is 0 or an integer 1 to 12;
when $R_b$ and $R_{1b}$ together is a bridging group linked to one or more further corresponding benzofuran(2)one or indolin(2)one nuclei, it is a group of the formulae

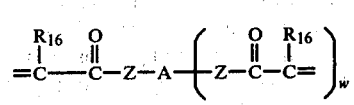
(e/9)

(e/12)

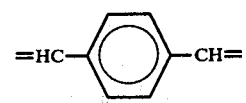
(e/13)

in which the free valencies are attached to one or more groups of the formula $E_{1a}$

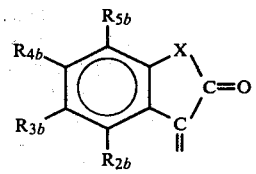
$E_{1a}$ wherein each of X, $R_{2b}$, $R_{3b}$, $R_{4b}$ and $R_{5b}$ is as defined in claim 3,
A, Z, w and $R_{10}$ are as defined above, whereby when A is a 3-, 4-, 5- or 6-valent saturated alkylene group, each further free valence is bound to —OH, —NHR$_{10}$ or a group of the formula

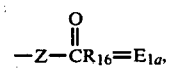

with the proviso that any free valence on nitrogen in A itself is attached to a group of the formula

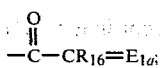

p is 0 or an integer 1 to 10; and
R$_{16}$ is hydrogen or methyl;
when R$_{3b}$ is a bridging group linked to one or more further corresponding benzofuran(2)one or indolin(2-)one nuclei, it is —O—, —S—, —SO$_2$—, >C=O,

where R$_{13}$ is as defined above, or a group (e/1) or (e/4) as defined above, in which the free valencies are attached to one or more groups of the formula E$_{3b}$

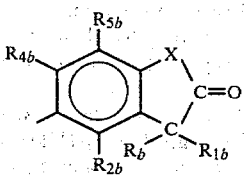

wherein each of X, R$_b$, R$_{1b}$, R$_{2b}$, R$_{4b}$ and R$_{5b}$ is as defined in claim 3, A, Z, w and R$_{10}$ are as defined above, whereby when A is a 3-, 4-, 5- or 6-valent saturated alkylene group, each further free valence is bound to —OH, —NHR$_{10}$ or a group of the formula

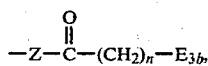

with the proviso that any free valence on nitrogen in A itself is attached to a group of the formula

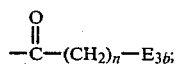

and
n is as defined in claim 3; or
when R$_{5b}$ is a bridging group linked to one or more further corresponding benzofuran(2)one or indolin(2-)one nuclei, it is —S—,

where R$_{13}$ is as defined above, or a group (e/1) or (e/4) as defined above, in which the free valencies are attached to one or more groups of the formula E$_{5b}$

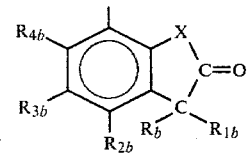

wherein each of X, R$_b$, R$_{1b}$, R$_{2b}$, R$_{3b}$ and R$_{4b}$ is as defined in claim 3, A, Z, w and R$_{10}$ are as defined above, whereby when A is a 3-, 4-, 5- or 6-valent saturated alkylene group, each further free valence is bound to —OH, —NHR$_{10}$ or a group of the formula

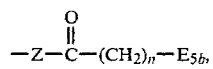

with the proviso that any free valence on nitrogen in A itself is attached to a group of the formula

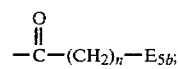

and
n is as defined in claim 3;
with the proviso that only one of R$_{1b}$, R$_b$ and R$_{1b}$ together, R$_{3b}$ or R$_{5b}$ is a polyvalent bridging group linked to one or more further corresponding benzofuran(2)one or indolin(2)one nuclei, the substituents in the nuclei being the same or different.

5. A process according to claim 4 wherein either (i) R$_a$ is (aa/1) and each R$_{1a}$ is R$_1$' where R$_1$' is hydrogen; C$_{1-18}$alkyl; phenyl; phenyl substituted by one to three substituents selected from C$_{1-8}$ alkyl and hydroxy, with the proviso that the maximum number of C$_{1-8}$ alkyl substituents is two and the maximum number of hydroxy substituents is one; or a group of formula (a/4) or (a/5);

or (ii) R$_a$ is hydrogen, X is —O— and R$_{1a}$ is a group of formula (a/7) where R$_{1ax}$ is phenyl or phenyl substituted by one to three substituents selected from C$_{1-8}$ alkyl and hydroxy, with the proviso that the maximum number of C$_{1-8}$ alkyl substituents is two and the maximum number of hydroxy substituents is one;

each of R$_{2a}$ and R$_{2b}$ is hydrogen or C$_{1-4}$ alkyl;
each R$_{3a}$ is R$_3$' where R$_3$' is hydrogen or C$_{1-9}$ alkyl;
each of R$_{4a}$ and R$_{4b}$ is hydrogen or C$_{1-4}$ alkyl;
each R$_{5a}$ is R$_5$' where R$_5$' is hydrogen or C$_{1-8}$ alkyl;
or (iii) R$_a$ is hydrogen, X is —O—, R$_{1a}$ is other than a group of formula (a/7) and either R$_{3a}$ is a group of formula (E$_3$) or R$_{5a}$ is a group of formula (E$_5$);
R$_b$ is hydrogen or together with R$_{1b}$ is a bridging group of the formula (e/9) or (e/13);
R$_{1b}$ is R$_{1bx}$ where R$_{1bx}$ is a significance as defined above for R$_1$' or is a bridging group of the formula (e/1), (e/4), (e/6), (e/7), (e/7a), (e/7b) or (e/8);
R$_{3b}$ is R$_{3bx}$ where R$_{3bx}$ is a significance as defined above for R$_3$' or is a bridging group of the formula —S—E$_{3b}$,

(e/1) or (e/4), where each $R_{13}'$, independently, is hydrogen, $C_{1-4}$ alkyl or a group of formula (a/4) in which $R_7$ is hydrogen or $C_{1-8}$ alkyl, with the proviso that when one of the $R_{13}'$'s is a group of formula (a/4), the other $R_{13}'$ is hydrogen or $C_{1-4}$ alkyl; $R_{5b}$ is $R_{5bx}$ where $R_{5bx}$ is a significance as defined above for $R_5'$ or is a bridging group of the formula $-S-E_{5b}$,

or (e/1), where each $R_{13}'$ is as defined above; and $R_{10}$ is hydrogen; $C_{1-12}$ alkyl or phenyl.

6. A process according to claim 5 in which any $R_1'$ is $C_{1-18}$ alkyl; phenyl or phenyl substituted by one to three substituents selected from $C_{1-8}$ alkyl and hydroxy, with the proviso that the maximum number of $C_{1-8}$ alkyl substituents is two and the maximum number of hydroxy substituents is one.

7. A process according to claim 1 comprising incorporating the benzofuran(2)one or indolin(2)one compound together with either (i) a stabilizer of the sterically hindered phenol type or (ii) a stabilizer of the thiodipropionate, thiopropionate, dialkylsulphide, aryl phosphite, aryl diphosphonite and tetraoxadiphosphaspiroundecane type, or (i) and (ii), into the polymeric material to be stabilized.

8. Polymeric organic material which contains, as the stabilizer, a benzofuran(2)one compound or indolin(2)one compound containing at least two benzofuran(2)one or indolin(2)one nuclei.

9. A process according to claim 4, in which when $R_{3b}$ or $R_{5b}$ is a bridging group, X is —O— in all cases.

10. A process according to claim 3, in which X is —O—.

11. A process according to claim 5, in which X is —O—.

12. A process according to claim 5, in which X is —O— and each benzofuran(2)one nucleus is identical with the exception of the case where $R_{1a}$ is (a/7) where $R_{1a}$ in the second nucleus is $R_{1ax}$.

13. A process according to claim 12, in which $R_a$ is (aa/1).

14. A process according to claim 12, in which $R_{1a}$ is (a/7).

15. A process according to claim 5, in which $R_b$ is hydrogen.

16. A process according to claim 1, in which the polymeric material is polypropylene, polyethylene, ethylene/propylene copolymers, PVC, polyesters, polyamides, polyurethanes, polyacrylonitrile, ABS terpolymers, terpolymers of acrylic ester, styrene and acrylonitrile, copolymers of styrene and acrylonitrile, styrene/butadiene copolymers, polybutylene or polystyrene.

17. A process according to claim 1, in which the polymeric material is polypropylene.

18. A process according to claim 1, in which the polymeric material is polyethylene or an ethylene/propylene copolymer.

19. A process according to claim 18, in which the polymeric material is high density (HD) polyethylene.

20. A process according to claim 1, in which from 0.01 to 5%, based on the weight of the polymeric material, of the benzofuran(2)one or indolin(2)one compound is incorporated in the polymeric material to be stabilised.

21. A process according to claim 1, in which the benzofuran(2)one or indolin(2)one compound is incorporated into the polymeric material by melt blending.

22. A process according to claim 1, in which 5 to 90% of the benzofuran(2)one or indolin(2)one compound is incorporated in the polymeric material to form a stabilized master batch.

23. A process according to claim 5, in which $R_{1b}$ is phenyl and $R_b$ is hydrogen.

24. A process according to claim 5, in which $R_{2a}$ and $R_{2b}$ are hydrogen.

* * * * *

UNITED STATES PATENT AND TRADEMARK OFFICE
CERTIFICATE OF CORRECTION

PATENT NO. : 4,338,244

DATED : July 6, 1982

INVENTOR(S) : HANS HINSKEN, ET AL.

It is certified that error appears in the above-identified patent and that said Letters Patent is hereby corrected as shown below:

Column 3, line 17; after "each", insert --, $R_7$,--.

Column 10, line 53; after "preferably", change "$R_a'$" to --$R_{3a}'$--.

Column 11, line 16; after "$R_7$", change "is" to --in--.

Column 11, line 22; after "Each", change "$E_8$" to --$R_8$--.

Column 13, to the right of the structural formula directly beneath line 15; change "III or $R_{3b}$" to --III for $R_{3b}$--.

Below Columns 17 and 18; directly beneath structural formula No. 1; change "m.pt. 87-188°" to --m.pt. 87-118°--.

Above Columns 19 and 20; delete structural formula No. 9 and substitute therefor

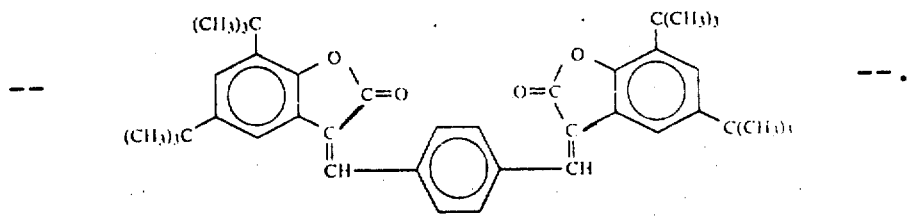

--.

UNITED STATES PATENT AND TRADEMARK OFFICE
CERTIFICATE OF CORRECTION

PATENT NO. : 4,338,244

DATED : July 6, 1982

INVENTOR(S) : HANS HINSKEN, ET AL.

It is certified that error appears in the above-identified patent and that said Letters Patent is hereby corrected as shown below:

Column 23, the line directly beneath structural formula Ia; after "is", change "-O-M" to -- -O- --.

Column 26; delete the structural formula at the bottom of the column and substitute therefor the formula

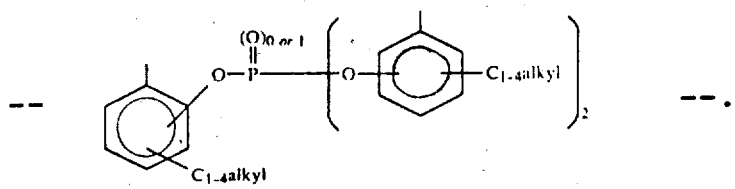

Column 31, line 10; after "or", change "$C_{1-8}$alkyl" to --$C_{1-18}$alkyl--.

Signed and Sealed this

Seventeenth Day of May 1983

[SEAL]

Attest:

DONALD J. QUIGG

Attesting Officer

Acting Commissioner of Patents and Trademarks